United States Patent
Barker

(10) Patent No.: US 8,214,054 B2
(45) Date of Patent: Jul. 3, 2012

(54) SYSTEMS AND METHODS FOR COUPLING CONDUCTORS TO CONDUCTIVE CONTACTS OF ELECTRICAL STIMULATION SYSTEMS

(75) Inventor: John Michael Barker, Ventura, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 228 days.

(21) Appl. No.: 12/419,763

(22) Filed: Apr. 7, 2009

(65) Prior Publication Data
US 2010/0256694 A1    Oct. 7, 2010

(51) Int. Cl.
*A61N 1/04* (2006.01)
(52) U.S. Cl. ......................... 607/115; 607/116
(58) Field of Classification Search ............ 607/46, 607/115–117, 119, 122; 600/372–374, 377, 600/378
See application file for complete search history.

(56) References Cited

U.S. PATENT DOCUMENTS

| | | | |
|---|---|---|---|
| 4,566,467 A | 1/1986 | DeHaan | |
| 4,590,950 A | 5/1986 | Iwaszkiewicz et al. | |
| 4,595,012 A * | 6/1986 | Webler et al. | 600/374 |
| 4,608,986 A | 9/1986 | Beranek et al. | |
| 4,744,371 A | 5/1988 | Harris | |
| 4,835,853 A | 6/1989 | Hirschberg et al. | |
| 4,938,822 A | 7/1990 | Peers-Trevarton | |
| 5,016,646 A * | 5/1991 | Gotthardt et al. | 607/122 |
| 5,324,321 A | 6/1994 | Pohndorf et al. | |
| 5,336,253 A | 8/1994 | Gordon et al. | |
| 5,425,755 A | 6/1995 | Doan | |
| 5,433,744 A | 7/1995 | Breyen et al. | |
| 5,458,629 A * | 10/1995 | Baudino et al. | 607/116 |
| 5,466,253 A | 11/1995 | Doan | |
| 5,514,172 A | 5/1996 | Mueller | |
| 5,522,872 A | 6/1996 | Hoff | |
| 5,713,944 A | 2/1998 | Kroll | |
| 5,796,044 A | 8/1998 | Cobian et al. | |

(Continued)

FOREIGN PATENT DOCUMENTS

EP        162178 A1    11/1985

(Continued)

OTHER PUBLICATIONS

U.S. Appl. No. 11/238,240, filed Sep. 29, 2005.

*Primary Examiner* — Carl H Layno
*Assistant Examiner* — Eugene Wu
(74) *Attorney, Agent, or Firm* — Frommer Lawrence & Haug LLP; Patrick R. Turner

(57) ABSTRACT

An electrical stimulation lead includes a plurality of conductive contacts disposed at a distal end and a proximal end of a lead body. The plurality of conductive contacts includes a plurality of electrodes and a plurality of terminals. At least one of the conductive contacts is a first conductive contact that includes at least one adhesive aperture defined between an inner surface and an outer surface of the at least one conductive contact. A plurality of conductors each electrically couple at least one of the electrodes to at least one of the terminals. Each first conductive contact has a conductor associated with, and electrically coupled to that first conductive contact. The adhesive is disposed in proximity to the at least one adhesive aperture of at least one first conductive contact to adhesively couple that first conductive contact to the at least one associated conductor.

17 Claims, 10 Drawing Sheets

U.S. PATENT DOCUMENTS

| | | | |
|---|---|---|---|
| 5,843,135 A | 12/1998 | Weijand et al. | |
| 5,869,804 A * | 2/1999 | Mueller et al. | 607/37 |
| 5,957,967 A | 9/1999 | Laske | |
| 5,968,086 A | 10/1999 | Bonner et al. | |
| 6,018,683 A | 1/2000 | Verness et al. | |
| 6,026,567 A | 2/2000 | Swoyer et al. | |
| 6,096,069 A | 8/2000 | Bischoff | |
| 6,104,961 A | 8/2000 | Conger et al. | |
| 6,181,969 B1 | 1/2001 | Gord | |
| 6,181,971 B1 | 1/2001 | Doan | |
| 6,249,708 B1 | 6/2001 | Nelson et al. | |
| 6,253,111 B1 | 6/2001 | Carner | |
| 6,295,476 B1 | 9/2001 | Schaenzer | |
| 6,366,820 B1 | 4/2002 | Doan et al. | |
| 6,501,991 B1 | 12/2002 | Honeck et al. | |
| 6,501,992 B1 | 12/2002 | Belden et al. | |
| 6,516,227 B1 | 2/2003 | Meadows et al. | |
| 6,609,029 B1 | 8/2003 | Mann et al. | |
| 6,609,032 B1 | 8/2003 | Woods et al. | |
| 6,687,549 B1 | 2/2004 | Helland et al. | |
| 6,697,675 B1 | 2/2004 | Safarevich et al. | |
| 6,741,892 B1 | 5/2004 | Meadows et al. | |
| 6,925,334 B1 | 8/2005 | Salys | |
| 6,973,351 B2 | 12/2005 | Morgan | |
| 6,978,185 B2 | 12/2005 | Osypka | |
| 6,999,821 B2 | 2/2006 | Jenney et al. | |
| 7,065,411 B2 | 6/2006 | Verness | |
| 7,138,582 B2 | 11/2006 | Lessar et al. | |
| 7,155,294 B2 | 12/2006 | Alinder | |
| 7,164,951 B2 | 1/2007 | Ries et al. | |
| 7,168,165 B2 | 1/2007 | Calzada et al. | |
| 7,184,840 B2 | 2/2007 | Stolz et al. | |
| 7,231,259 B2 | 6/2007 | Jenney et al. | |
| 7,239,922 B1 | 7/2007 | Boogaard et al. | |
| 7,244,150 B1 | 7/2007 | Brase et al. | |
| 7,292,894 B2 | 11/2007 | Belden | |
| 7,310,873 B2 | 12/2007 | Pardo et al. | |
| 7,489,971 B1 * | 2/2009 | Franz | 607/116 |
| 7,546,165 B2 | 6/2009 | Zarembo et al. | |
| 2003/0114905 A1 | 6/2003 | Kuzma | |
| 2003/0199951 A1 | 10/2003 | Pardo et al. | |
| 2004/0055776 A1 | 3/2004 | Milijasevic | |
| 2004/0059392 A1 | 3/2004 | Parramon et al. | |
| 2004/0172117 A1 | 9/2004 | Hill et al. | |
| 2005/0027340 A1 | 2/2005 | Schrom et al. | |
| 2005/0033397 A1 | 2/2005 | Aisenbrey | |
| 2005/0165465 A1 | 7/2005 | Pianca et al. | |
| 2006/0089691 A1 | 4/2006 | Kaplan et al. | |
| 2006/0190067 A1 | 8/2006 | Wengreen et al. | |
| 2006/0206185 A1 | 9/2006 | Schuller | |
| 2006/0229693 A1 | 10/2006 | Bauer et al. | |
| 2007/0150007 A1 | 6/2007 | Anderson et al. | |
| 2007/0150036 A1 | 6/2007 | Anderson | |
| 2007/0154729 A1 | 7/2007 | Chastain et al. | |
| 2007/0161294 A1 | 7/2007 | Brase et al. | |
| 2007/0168007 A1 * | 7/2007 | Kuzma et al. | 607/116 |
| 2007/0219595 A1 | 9/2007 | He | |
| 2007/0239243 A1 | 10/2007 | Moffitt et al. | |
| 2007/0239245 A1 | 10/2007 | Borgaonkar et al. | |
| 2007/0250143 A1 | 10/2007 | Sommer | |
| 2008/0046051 A1 | 2/2008 | Skubitz et al. | |
| 2008/0071320 A1 | 3/2008 | Brase | |
| 2008/0167701 A1 | 7/2008 | John et al. | |
| 2008/0178449 A1 | 7/2008 | Huotari et al. | |
| 2008/0262584 A1 | 10/2008 | Bottomley et al. | |
| 2008/0269863 A1 | 10/2008 | Alexander et al. | |
| 2009/0012591 A1 | 1/2009 | Barker | |
| 2009/0082655 A1 | 3/2009 | Seifert et al. | |
| 2009/0149933 A1 | 6/2009 | Ameri | |

FOREIGN PATENT DOCUMENTS

| | | |
|---|---|---|
| EP | 0343402 A2 | 11/1989 |
| EP | 1354610 A1 | 10/2003 |
| EP | 1528946 | 5/2005 |
| EP | 1545694 A1 | 6/2005 |
| EP | 2051772 | 4/2009 |
| EP | 2063957 | 6/2009 |
| WO | WO-01/91851 A1 | 12/2001 |
| WO | WO-02/49716 A1 | 6/2002 |
| WO | WO-02/083234 A1 | 10/2002 |
| WO | WO-2009/023017 A1 | 2/2009 |

* cited by examiner

SYSTEMS AND METHODS FOR COUPLING CONDUCTORS TO CONDUCTIVE CONTACTS OF ELECTRICAL STIMULATION SYSTEMS

FIELD

The present invention is directed to the area of implantable electrical stimulation systems and methods of making and using the systems. The present invention is also directed to improved systems and methods for coupling conductors to conductive contacts of implantable electrical stimulation leads (or lead extensions), as well as methods of making and using the conductive contacts and electrical stimulation systems.

BACKGROUND

Implantable electrical stimulation systems have proven therapeutic in a variety of diseases and disorders. For example, spinal cord stimulation systems have been used as a therapeutic modality for the treatment of chronic pain syndromes. Peripheral nerve stimulation has been used to treat chronic pain syndrome and incontinence, with a number of other applications under investigation. Functional electrical stimulation systems have been applied to restore some functionality to paralyzed extremities in spinal cord injury patients.

Stimulators have been developed to provide therapy for a variety of treatments. A stimulator can include a control module (with a pulse generator), one or more leads, and an array of stimulator electrodes on each lead. The stimulator electrodes are in contact with or near the nerves, muscles, or other tissue to be stimulated. The pulse generator in the control module generates electrical pulses that are delivered by the electrodes to body tissue.

BRIEF SUMMARY

In one embodiment, an electrical stimulation lead includes a lead body, a plurality of conductive contacts, and an adhesive. The lead body has a proximal end, a distal end, and a longitudinal length. The plurality of conductive contacts are disposed at the distal end and the proximal end of the lead body. The plurality of conductive contacts includes a plurality of electrodes and a plurality of terminals. The plurality of electrodes are disposed on the distal end of the lead. The plurality of terminals are disposed on the proximal end of the lead. At least one of the conductive contacts is a first conductive contact that includes at least one adhesive aperture defined between an inner surface and an outer surface of the at least one conductive contact. The plurality of conductors each electrically couple at least one of the electrodes to at least one of the terminals. Each first conductive contact has at least one of the conductors associated with, and electrically coupled to that first conductive contact. The adhesive is disposed in proximity to the at least one adhesive aperture of at least one first conductive contact to adhesively couple that first conductive contact to the at least one associated conductor.

In another embodiment, an electrical stimulation system includes an electrical stimulation lead, a control module, and a connector for receiving the lead. The electrical stimulation lead includes a lead body, a plurality of conductive contacts, and an adhesive. The lead body has a proximal end, a distal end, and a longitudinal length. The plurality of conductive contacts are disposed at the distal end and the proximal end of the lead body. The plurality of conductive contacts includes a plurality of electrodes and a plurality of terminals. The plurality of electrodes are disposed on the distal end of the lead. The plurality of terminals are disposed on the proximal end of the lead. At least one of the conductive contacts is a first conductive contact that includes at least one adhesive aperture defined between an inner surface and an outer surface of the at least one conductive contact. The plurality of conductors each electrically couple at least one of the electrodes to at least one of the terminals. Each first conductive contact has at least one of the conductors associated with, and electrically coupled to that first conductive contact. The adhesive is disposed in proximity to the at least one adhesive aperture of at least one first conductive contact to adhesively couple that first conductive contact to the at least one associated conductor. The control module configured and arranged to electrically couple to the proximal end of the lead. The control module including a housing and an electronic subassembly disposed in the housing. The connector having a proximal end, a distal end, and a longitudinal length. The connector configured and arranged to receive the lead. The connector including a connector housing and a plurality of connector contacts disposed in the connector housing. The connector housing defining a port at the distal end of the connector. The port configured and arranged for receiving the proximal end of the lead. The connector contacts configured and arranged to couple to at least one of the plurality of terminals disposed on the proximal end of the lead.

In yet another embodiment, a method for forming an electrical stimulation lead includes coupling a plurality of spaced-apart conductive contacts to either end of a lead body. The conductive contacts are separated from one another by spacers. The plurality of conductive contacts include electrodes disposed on a distal end of the lead body and a plurality of terminals disposed on a proximal end of the lead body. At least one of the conductive contacts is a first conductive contact that includes at least one adhesive aperture defined between an inner surface and an outer surface of the at least one conductive contact. The electrodes are electrically coupled to the terminals via conductors. At least one of the conductors is associated, and electrically coupled, to the at least one first conductive contact. An adhesive is dispensed over the at least one adhesive aperture to adhesively couple the at least one first connective contact to the at least one associated conductor.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

The present invention is directed to the area of implantable electrical stimulation systems and methods of making and using the systems. The present invention is also directed to improved systems and methods for coupling conductors to conductive contacts of implantable electrical stimulation leads (or lead extensions), as well as methods of making and using the conductive contacts and electrical stimulation systems.

Suitable implantable electrical stimulation systems include, but are not limited to, an electrode lead ("lead") with one or more electrodes disposed on a distal end of the lead and one or more terminals disposed on one or more proximal ends of the lead. Leads include, for example, percutaneous leads, paddle leads, and cuff leads. Examples of electrical stimulation systems with leads are found in, for example, U.S. Pat. Nos. 6,181,969; 6,516,227; 6,609,029; 6,609,032; and 6,741,892; and U.S. patent applications Ser. Nos. 10/353,101, 10/503,281, 11/238,240; 11/319,291; 11/327,880; 11/375,638; 11/393,991; and 11/396,309, all of which are incorporated by reference.

Figure 1:
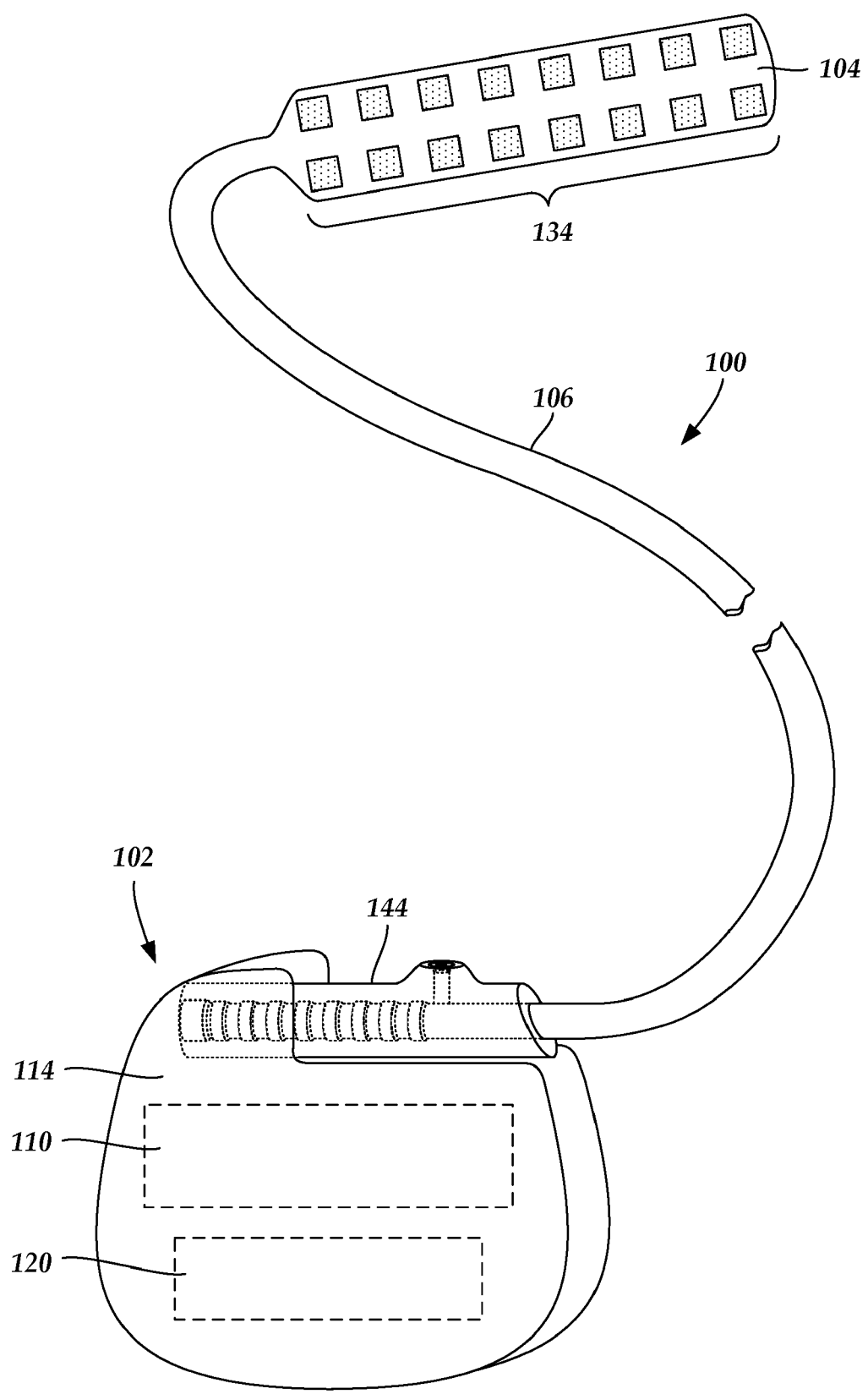
FIG. 1 is a schematic view of one embodiment of an electrical stimulation system, according to the invention.
Figure 2:
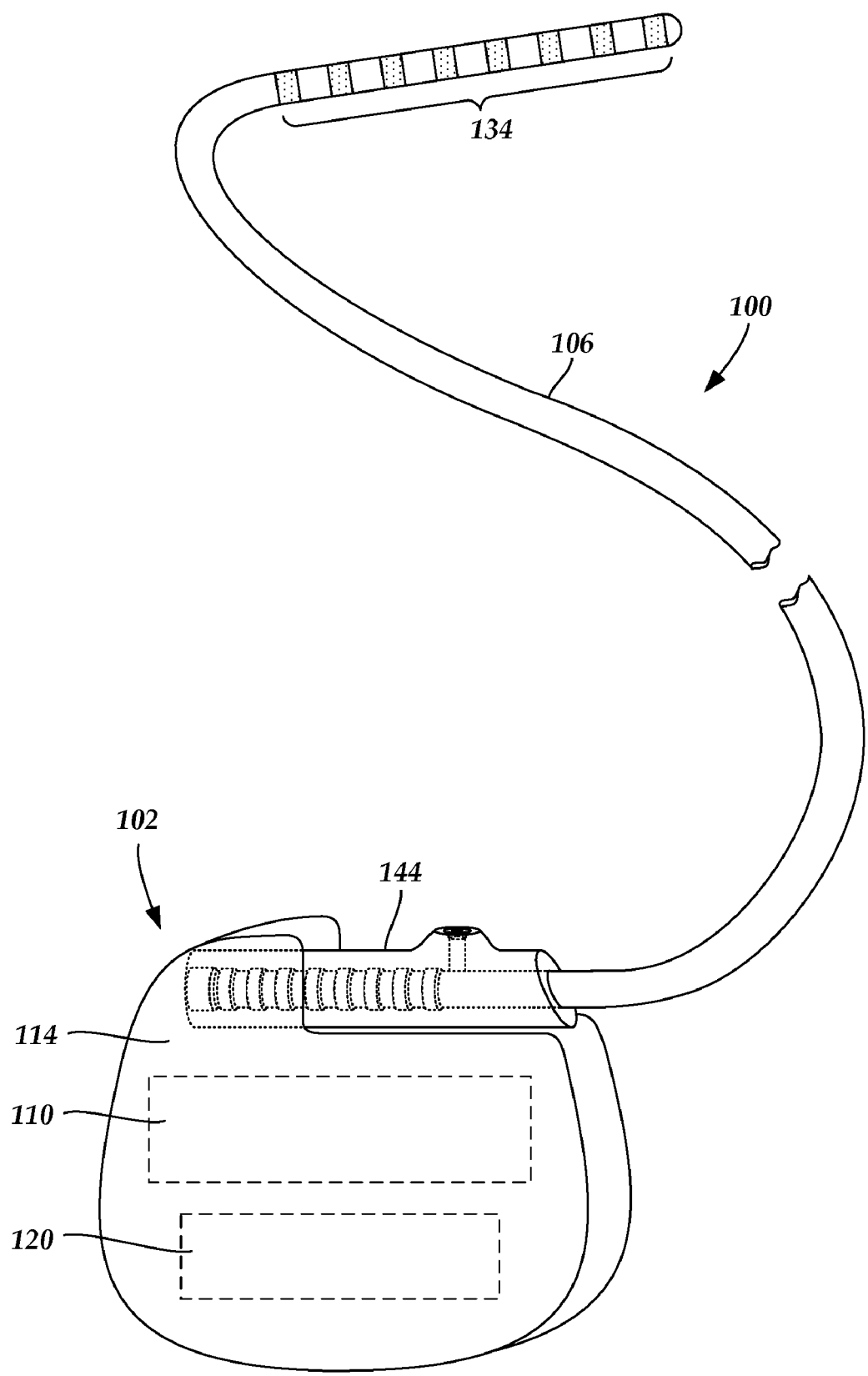
FIG. 2 is a schematic view of another embodiment of an electrical stimulation system, according to the invention.

FIG. 1 illustrates schematically one embodiment of an electrical stimulation system 100. The electrical stimulation system includes a control module (e.g., a stimulator or pulse generator) 102, a paddle body 104, and at least one lead body 106 coupling the control module 102 to the paddle body 104. The paddle body 104 and the one or more lead bodies 106 form a lead. The paddle body 104 typically includes an array of electrodes 134. The control module 102 typically includes an electronic subassembly 110 and an optional power source 120 disposed in a sealed housing 114. The control module 102 typically includes a connector 144 (FIG. 2 and 3A, see also 322 and 350 of FIG. 3B) into which the proximal end of the one or more lead bodies 106 can be plugged to make an electrical connection via conductive contacts on the control module 102 and terminals (e.g., 310 in FIG. 3A and 336 of FIG. 3B) on each of the one or more lead bodies 106. It will be understood that the electrical stimulation system can include more, fewer, or different components and can have a variety of different configurations including those configurations disclosed in the electrical stimulation system references cited herein. For example, instead of a paddle body 104, the electrodes 134 can be disposed in an array at or near the distal end of the lead body 106 forming a percutaneous lead, as illustrated in FIG. 2. A percutaneous lead may be isodiametric along the length of the lead. In addition, one or more lead extensions 312 (see FIG. 3B) can be disposed between the one or more lead bodies 106 and the control module 102 to extend the distance between the one or more lead bodies 106 and the control module 102 of the embodiments shown in FIGS. 1 and 2.

The electrical stimulation system or components of the electrical stimulation system, including one or more of the lead bodies 106, the paddle body 104, and the control module 102, are typically implanted into the body of a patient. The electrical stimulation system can be used for a variety of applications including, but not limited to, brain stimulation, neural stimulation, spinal cord stimulation, muscle stimulation, and the like.

The electrodes 134 can be formed using any conductive, biocompatible material. Examples of suitable materials include metals, alloys, conductive polymers, conductive carbon, and the like, as well as combinations thereof. The number of electrodes 134 in the array of electrodes 134 may vary. For example, there can be two, four, six, eight, ten, twelve, fourteen, sixteen, or more electrodes 134. As will be recognized, other numbers of electrodes 134 may also be used.

The electrodes of the paddle body 104 or one or more lead bodies 106 are typically disposed in, or separated by, a non-conductive, biocompatible material including, for example, silicone, polyurethane, polyetheretherketone ("PEEK"), epoxy, and the like or combinations thereof. The paddle body 104 and one or more lead bodies 106 may be formed in the desired shape by any process including, for example, molding (including injection molding), casting, and the like. Electrodes and connecting wires can be disposed onto or within a paddle body either prior to or subsequent to a molding or casting process. The non-conductive material typically extends from the distal end of the lead to the proximal end of each of the one or more lead bodies 106. The non-conductive, biocompatible material of the paddle body 104 and the one or more lead bodies 106 may be the same or different. The paddle body 104 and the one or more lead bodies 106 may be a unitary structure or can be formed as two separate structures that are permanently or detachably coupled together.

Terminals (e.g., 310 in FIG. 3A and 336 of FIG. 3B) are typically disposed at the proximal end of the one or more lead bodies 106 for connection to corresponding conductive contacts (e.g., 314 in FIG. 3A and 340 of FIG. 3B) in connectors (e.g., 144 in FIGS. 1-3A and 322 and 350 of FIG. 3B) disposed on, for example, the control module 102 (or to other devices, such as conductive contacts on a lead extension, an operating room cable, or an adaptor). Conductive wires ("conductors") (not shown) extend from the terminals (e.g., 310 in FIG. 3A and 336 of FIG. 3B) to the electrodes 134. Typically, one or more electrodes 134 are electrically coupled to a terminal (e.g., 310 in FIG. 3A and 336 of FIG. 3B). In some embodiments, each terminal (e.g., 310 in FIG. 3A and 336 of FIG. 3B) is only connected to one electrode 134. The conductors may be embedded in the non-conductive material of the lead or can be disposed in one or more lumens (see e.g., FIGS. 4A-4B) extending along the lead. In some embodiments, there is an individual lumen for each conductor. In other embodiments, two or more conductors may extend through a lumen. There may also be one or more lumens (not shown) that open at, or near, the proximal end of the lead, for example, for inserting a stylet rod to facilitate placement of the lead within a body of a patient. Additionally, there may also be one or more lumens (not shown) that open at, or near, the distal end of the lead, for example, for infusion of drugs or medication into the site of implantation of the paddle body 104. In at least one embodiment, the one or more lumens may be flushed continually, or on a regular basis, with saline, epidural fluid, or the like. In at least some embodiments, the one or more lumens can be permanently or removably sealable at the distal end.

Figure 3A:
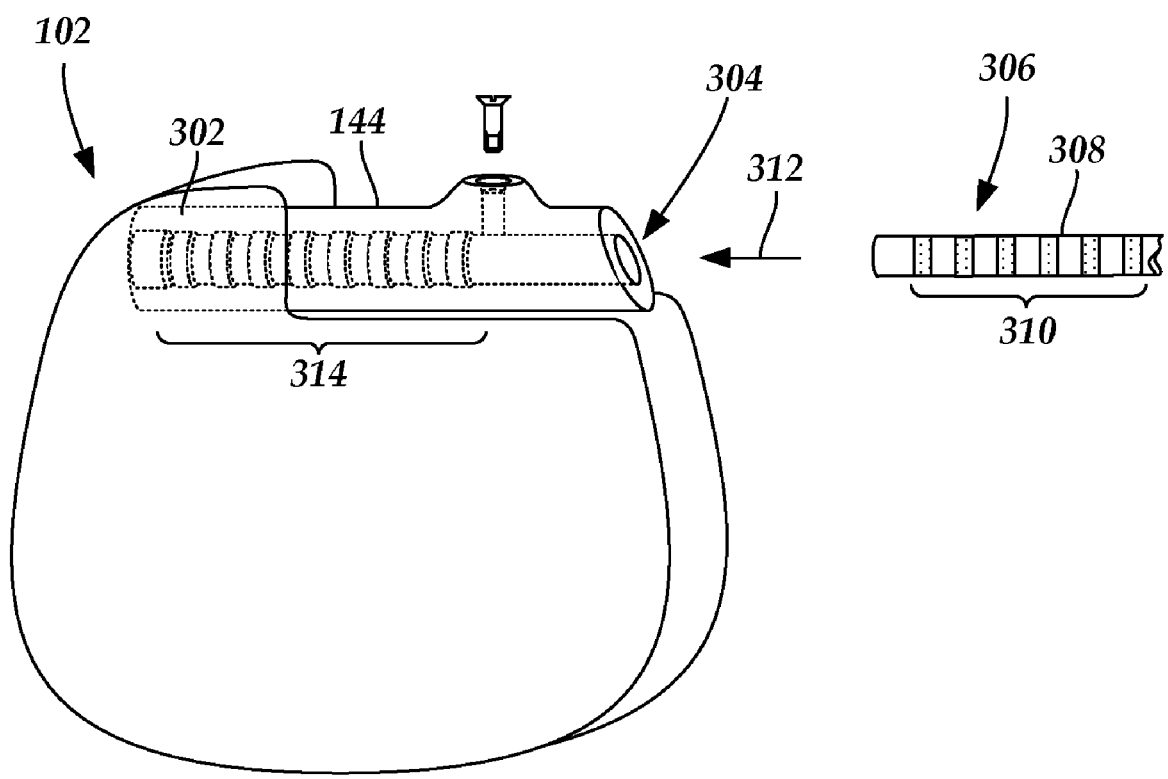
FIG. 3A is a schematic view of one embodiment of a proximal portion of a lead and a control module of an electrical stimulation system, according to the invention.

In at least some embodiments, leads are coupled to connectors disposed on control modules. In FIG. 3A, a lead 308 is shown configured and arranged for insertion to the control module 102. The connector 144 includes a connector housing 302. The connector housing 302 defines at least one port 304 into which a proximal end 306 of a lead 308 with terminals 310 can be inserted, as shown by directional arrow 312. The connector housing 302 also includes a plurality of conductive contacts 314 for each port 304. When the lead 308 is inserted into the port 304, the conductive contacts 314 can be aligned with the terminals 310 on the lead 308 to electrically couple the control module 102 to the electrodes (134 of FIG. 1) disposed at a distal end of the lead 308. Examples of connectors in control modules are found in, for example, U.S. Pat. No. 7,244,150 and U.S. patent application Ser. No. 11/532,844, which are incorporated by reference.

Figure 3B:
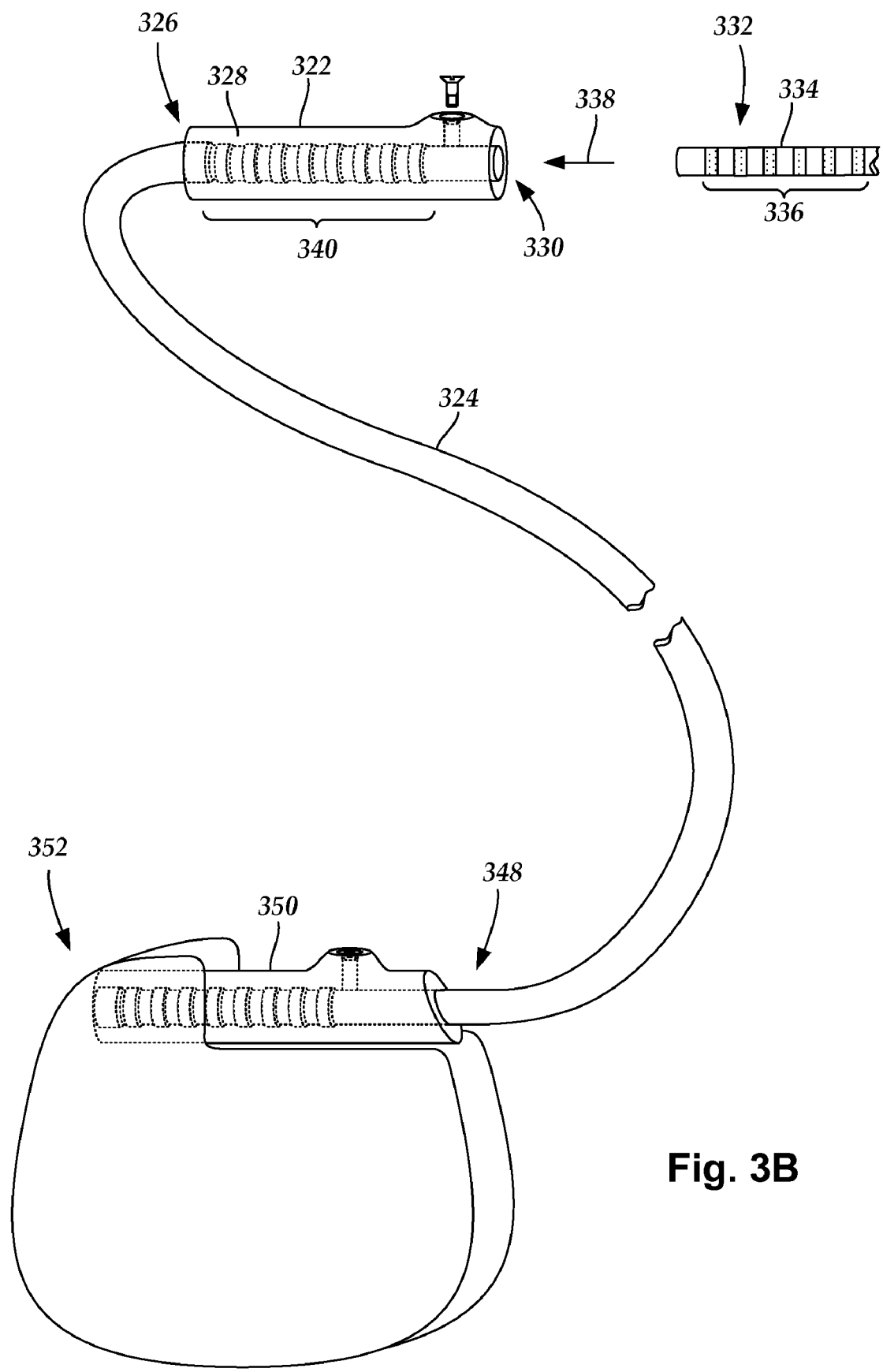
FIG. 3B is a schematic view of one embodiment of a proximal portion of a lead and a lead extension of an electrical stimulation system, according to the invention.

In FIG. 3B, a connector 322 is disposed on a lead extension 324. The connector 322 is shown disposed at a distal end 326 of the lead extension 324. The connector 322 includes a connector housing 328. The connector housing 328 defines at least one port 330 into which a proximal end 332 of a lead 334 with terminals 336 can be inserted, as shown by directional arrow 338. The connector housing 328 also includes a plurality of conductive contacts 340. When the lead 334 is inserted into the port 330, the conductive contacts 340 disposed in the connector housing 328 can be aligned with the terminals 336 on the lead 334 to electrically couple the lead extension 324 to the electrodes (134 of FIG. 1) disposed at a distal end (not shown) of the lead 334.

In at least some embodiments, the proximal end of a lead extension is similarly configured and arranged as a proximal end of a lead. The lead extension 324 may include a plurality of conductive wires (not shown) that electrically couple the conductive contacts 340 to a proximal end 348 of the lead extension 324 that is opposite to the distal end 326. In at least some embodiments, the conductive wires disposed in the lead extension 324 can be electrically coupled to a plurality of terminals (not shown) disposed on the proximal end 348 of the lead extension 324. In at least some embodiments, the proximal end 348 of the lead extension 324 is configured and arranged for insertion into a connector disposed in another lead extension. In other embodiments, the proximal end 348 of the lead extension 324 is configured and arranged for insertion into a connector disposed in a control module. As an example, in FIG. 3B the proximal end 348 of the lead extension 324 is inserted into a connector 350 disposed in a control module 352.

Figure 4A:
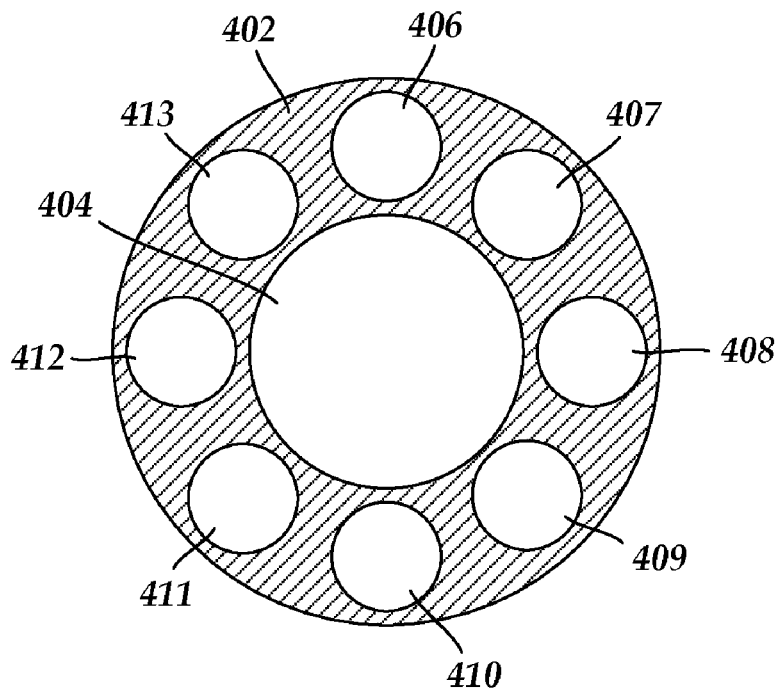
FIG. 4A is a schematic transverse cross-sectional view of one embodiment of a conductor-carrying element of a lead (or lead extension), the conductor-carrying element defining lumens, according to the invention.

Conductors may be disposed within a body of an elongated member (e.g., a lead, lead extension, or the like) in any number of different arrangements. FIG. 4A is a schematic transverse cross-sectional view of one embodiment of a conductor-carrying element 402 that may extend along at least a portion of a longitudinal length of a body of an elongated member. The conductor-carrying element 402 defines multiple lumens. For example, in FIG. 4A, and in other figures, the conductor-carrying element 402 defines a central lumen 404 and conductor lumens 406-413. It will be understood that some embodiments may not include the central lumen 404. In at least some embodiments, the conductor-carrying element 402 may additionally include one or more layers of material disposed over or around one or more portions of the conductor-carrying element 402.

Figure 4B:
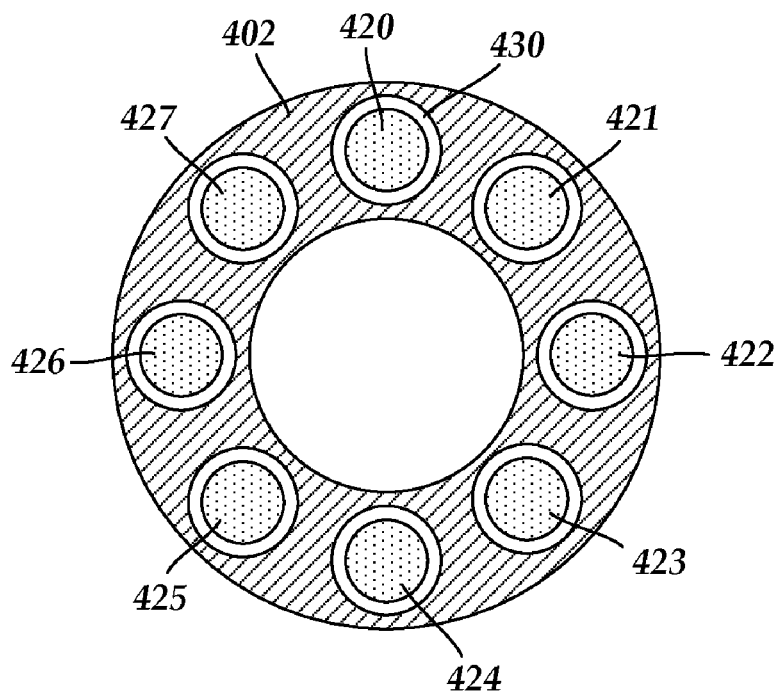
FIG. 4B is a schematic transverse cross-sectional view of one embodiment of conductors disposed in lumens of the conductor-carrying element of FIG. 4A, according to the invention.

In at least some embodiments, one or more conductors extend along at least a portion of a longitudinal length of the conductor-carrying element 402 within one of the conductor lumens 406-413. FIG. 4B is a schematic transverse cross-sectional view of one embodiment of conductors 420-427 disposed in the conductor-carrying element 402. In at least some embodiments, insulation 430 is disposed around a longitudinal length of one or more of the conductors 420-427.

In at least some embodiments, ends of the conductors 420-427 are coupled to conductive contacts (e.g., electrodes, terminals, or the like). For example, one set of ends of the conductors 420-427 disposed in a lead may couple to electrodes (e.g., electrodes 134 of FIGS. 1 and 2) and the opposing set of ends of the conductors 420-427 may couple to terminals (e.g., terminals 310 of FIG. 3A and 336 of FIG. 3B). It will be understood that conductors may, alternatively, extend along bodies with different lumen arrangements, as well as bodies that do not define lumens at all. In some embodiments, one or more lumens may house multiple conductors. In other embodiments, one or more lumens may not house any conductors.

Conductors can be formed using any conductive, biocompatible material. Examples of suitable materials include metals, alloys, conductive polymers, conductive carbon, and the like, as well as combinations thereof. For example, in at least some embodiments, conductors are formed from silver and nickel-cobalt-chromium-molybdenum alloy. Conductors are typically electrically coupled to conductive contacts (e.g., electrodes, terminals, or the like) by welding (e.g., laser, resistance, or the like), soldering, mechanical deformation, or the like. In at least some embodiments, conductors may be multi-filar and arranged in many different configurations (e.g., 1×7, 1×19, and the like). Conductors may be formed from many different gauges.

Conductors may be exposed to various forces associated with implantation and patient movement after implantation. Accordingly, it is preferred that conductors, and the bonds between the conductors and the conductive contacts, have adequate strength to be able to withstand these forces. One way to increase strength is to increase the outer diameters of conductors. However, it is also preferred to form bodies of elongated members with outer diameters that are as small as possible to facilitate implantation into patients.

In addition to employing conductors with adequate strength, it is also a concern to provide a coupling between conductors and conductive contacts with a pull strength (i.e., the ability to withstand pulling on the conductor without the conductor uncoupling from the conductive contact) that is strong enough to withstand the various forces mentioned above. Unfortunately, conventional coupling techniques may not provide adequate pull strength to reliably maintain a coupling between conductors and conductive contacts.

A conductive contact (e.g., an electrode, a terminal, or the like) may define one or more adhesive apertures along a longitudinal length of the conductive contact. When the conductive contact is disposed at one end of an elongated member (e.g., a lead, lead extension, or the like) and a conductor is electrically coupled to the conductive contact, a curable adhesive may be passed through one or more of the adhesive apertures and allowed to cure, thereby coupling the conductor to the elongated member, the conductive contact, or both. In at least some embodiments, the adhesive provides additional pull strength to the coupling between the conductor and the conductive contact.

Figure 5:
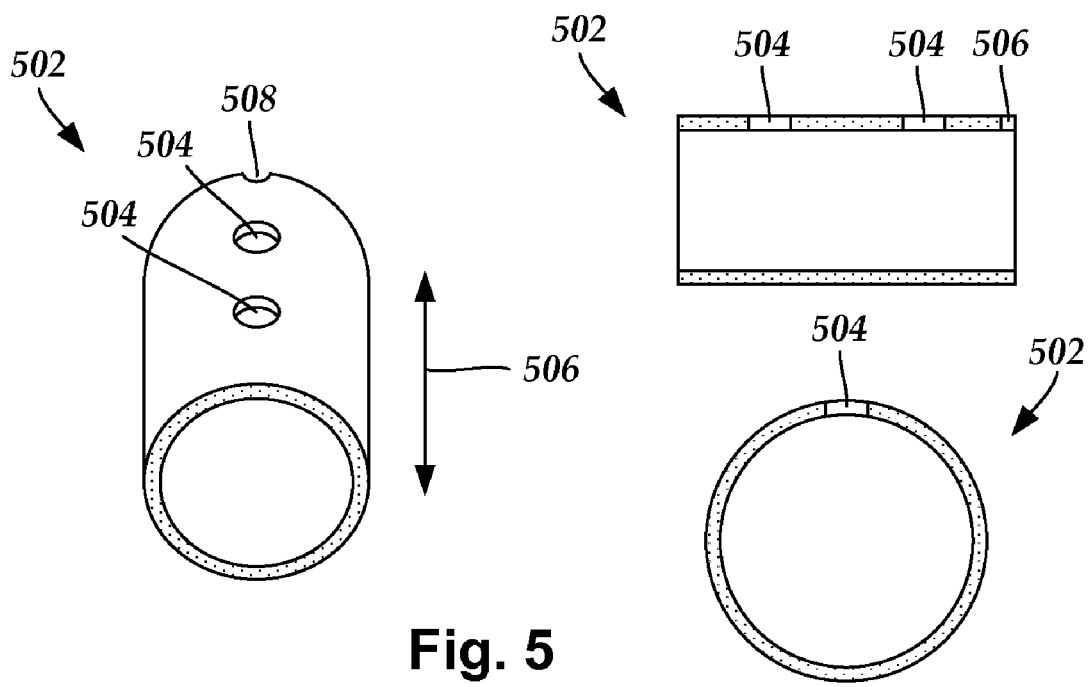
FIG. 5 is a schematic perspective, longitudinal cross-sectional, and transverse cross-sectional view of one embodiment of a conductive contact configured and arranged for coupling to a lead (or lead extension), according to the invention.

FIG. 5 is a schematic perspective, longitudinal cross-sectional, and transverse cross-sectional view of one embodiment of a conductive contact 502. The conductive contact 502 includes adhesive apertures 504 defined along a longitudinal length (represented by arrow 506). In at least some embodiments, the conductive contact 502 has a cylindrical shape. In at least some embodiments, the conductive contact is C-shaped. In at least some embodiments, a diameter of the conductive contact 502 is no greater than the longitudinal length 506 of the conductive contact 502.

There may be any number of adhesive apertures 504. For example, there may be one, two, three, four, five, six, seven, eight, nine, ten, or more adhesive apertures 504. It will be understood that there may be other numbers of adhesive apertures 504, as well. The adhesive apertures 504 may be of any size or shape. In preferred embodiments, at least one of the adhesive apertures 504 is large enough that an adhesive can be input through the adhesive aperture 504. In at least some embodiments, the adhesive apertures 504 are formed by drilling (e.g., laser cutting, conventional drilling, or the like) one or more holes through the conductive contact 502. In at least some embodiments, the adhesive apertures 504 are burned through the conductive contact 502 using electro-discharge machining. In at least some embodiments, there are at least two adhesive apertures where adhesive can be input into one aperture and displaced air can escape through another aperture.

In at least some embodiments, the conductive contact 502 also defines at least one contact aperture 508. The contact aperture 508 may be of any size or shape. In at least some embodiments, the contact aperture 508 is positioned in proximity to one of the edges (or ends) of the contact aperture 508 (see e.g., FIG. 7). In at least some embodiments, the contact aperture 508 is a notch defined in one end of the conductive contact 502. In preferred embodiments, the contact aperture 508 is large enough that underlying conductors can be blind welded to the conductive contact 502 via the contact aperture 508. In at least some embodiments, at least one of the adhesive apertures 504 is longitudinally aligned with the contact aperture 508 along the longitudinal length 506 of the conductive contact 502. It may be an advantage to align the adhesive apertures 504 with the contact aperture 508 so that, after welding the underlying conductor to the conductive contact 502, the underlying conductor is centered under the adhesive apertures 504.

In at least some embodiments, the contact aperture 508 is positioned in proximity to a lateral end of the conductive contact 502. In other words, when the conductive contact 502 is an electrode disposed on a distal end of a lead, in at least some embodiments the contact aperture 508 is positioned in proximity to a distal end of the electrode. Similarly, when the conductive contact is a terminal disposed on a proximal end of a lead (or lead extension), in at least some embodiments the contact aperture 508 is positioned in proximity to a proximal end of the terminal.

Figure 6A:
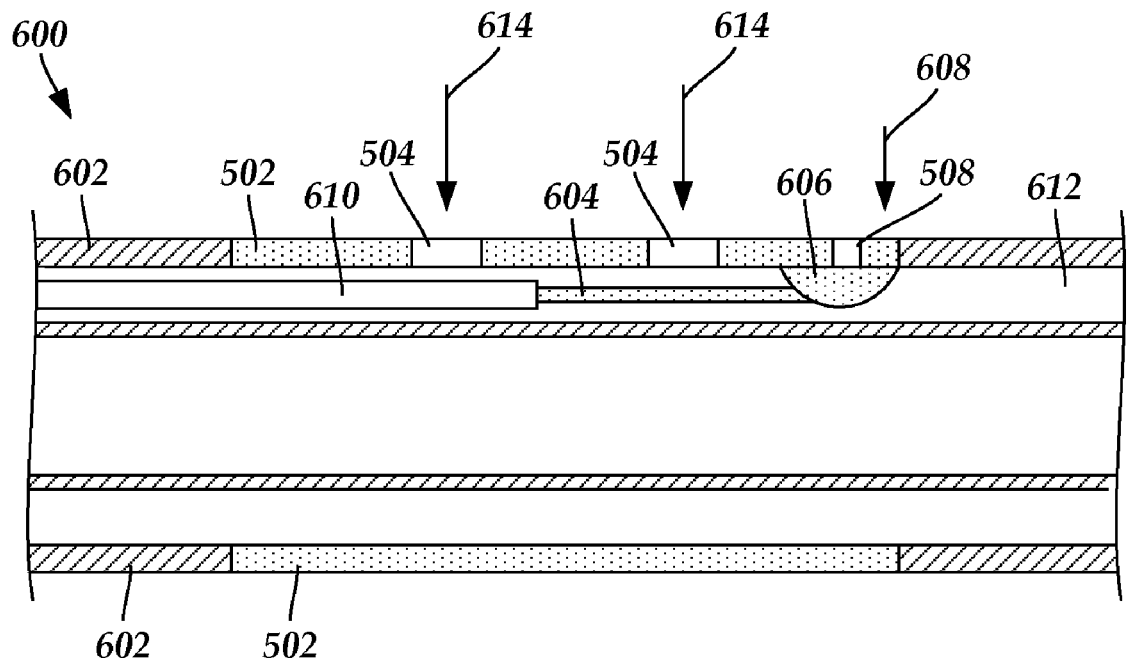
FIG. 6A is a schematic longitudinal cross-sectional view of one embodiment of the conductive contact of FIG. 5 disposed over an outer portion of a lead (or lead extension), the conductive contact electrically coupled to a conductor disposed within the lead (or lead extension), according to the invention.

FIG. 6A is a schematic longitudinal cross-sectional view of one embodiment of a portion of a body 602 of an elongated member 600. The conductive contact 502 is disposed along an outer surface of the body 602. A conductor 604 is disposed in the body 602 and is electrically coupled to the conductive contact 502. In at least some embodiments, the conductor 604 is electrically coupled to the conductive contact via one or more welds 606 (e.g., formed by resistance welding, laser welding, or the like). Other methods of attaching the conductor to the conductive contact can also be used. In at least some embodiments, the welding 606 is performed via the contact aperture 508, as shown by directional arrow 608.

In at least some embodiments, insulation 610 is disposed around the conductor 604. In at least some embodiments, the insulation 610 is removed at the portion of the conductor 604 electrically coupled to the conductive contact 502. In at least some embodiments, the conductor 604 is disposed in a lumen 612 defined in the body 602, such as one of the lumens (406-413 of FIG. 4A) of the conductor-carrying element (402 in FIG. 4).

Typically, the conductor 604 is electrically coupled to the conductive contact 502 such that the conductor 604 extends beneath at least one of the adhesive apertures 504. In at least some embodiments, the conductor 604 is electrically coupled to the conductive contact 502 at (or in proximity to) a lateral end (or edge) of the conductive contact 502 (i.e., a distal end of an electrode or a proximal end of a terminal).

In at least some embodiments, an adhesive may be input (e.g., injected, poured, pumped, flowed, or the like) through one or more of the adhesive apertures 504, as shown by directional arrows 614. In preferred embodiments, the adhesive flows during application and subsequently cures, sets, or cross-links (or any combination thereof), thereby coupling the conductor 604 to the conductive contact 502, the body 602, or both. In at least some embodiments, the adhesive mechanically couples the conductor 604 to the conductive contact 502, the body 602, or both. In at least some embodiments, the adhesive is electrically conductive and electrically couples the conductor 604 to the conductive contact 502, the body 602, or both. In at least some embodiments, the adhesive is input through one or more of the adhesive apertures 504 such that air is allowed to evacuate the region of the body 602 into which the adhesive is input via one or more of the other adhesive apertures 504.

Figure 6B:
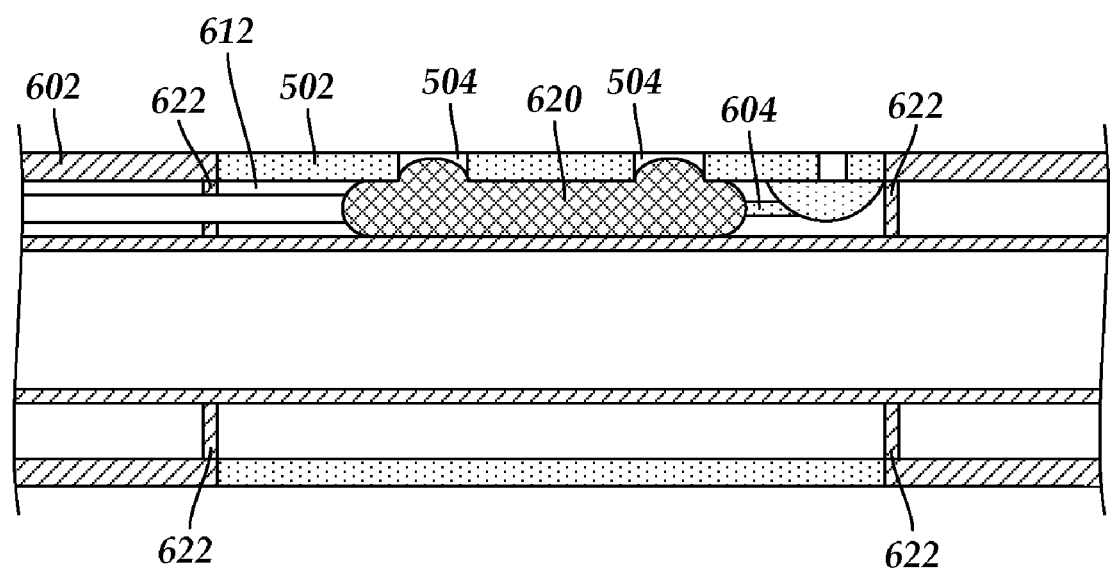
FIG. 6B is a schematic longitudinal cross-sectional view of one embodiment of the conductive contact of FIG. 5 disposed over an outer portion of the lead (or lead extension) of FIG. 6A and electrically coupled to a conductor disposed within the lead (or lead extension), the conductor also coupled to the lead (or lead extension), the conductive contact, or both, by an adhesive input through adhesive apertures defined in the conductive contact, according to the invention.

FIG. 6B is a schematic longitudinal cross-sectional view of one embodiment of an adhesive 620 input through the adhesive apertures 504 and cured within the body 602. Many different types of biocompatible adhesives may be used including, for example, natural adhesives, synthetic adhesives, drying adhesives, contact adhesives, light curing adhesives, pressure curing adhesives, reactive adhesives, or the like or combinations thereof. In at least some embodiments, the adhesive is an epoxy (e.g., a two-part thermoset epoxy adhesive, or the like). In at least some embodiments, a pull strength of the coupling of the conductor 604 to the body 602, the conductive contact 502, or both, by the adhesive 620 is no less than a tensile strength of the conductor 604.

In at least some embodiments, a plurality of spaced-apart conductive contacts are disposed at one end of the body 602. Each of the conductive contacts are electrically coupled to a different conductor disposed in the body 602. In at least some embodiments, adjacent conductive contacts are separated from one another by non-conductive spacers. In at least some embodiments, the spacers are formed from polyurethane.

In at least some embodiments, the conductive contacts and intervening spacers are reflowed together. In at least some embodiments, when the body 602 defines lumens, the reflowing process seals the lumens at the ends of the conductive contacts. Accordingly, in at least some embodiments, the adhesive 620 input through the adhesive apertures 504 is contained in the lumen 612 housing the conductor 604 such that the adhesive 620 is prevented from flowing beyond either end of the conductive contact 502 by seals 622 formed during the reflow process.

Figure 7:
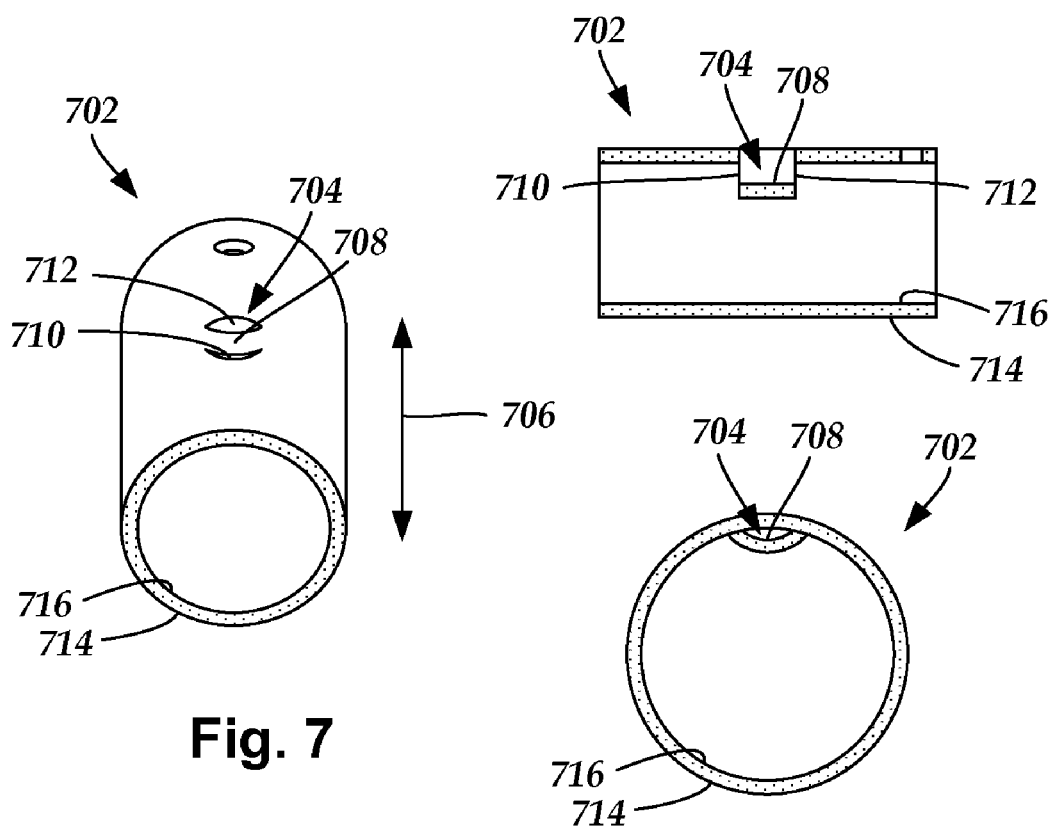
FIG. 7 is a schematic perspective, longitudinal cross-sectional, and transverse cross-sectional view of another embodiment of a conductive contact configured and arranged for coupling to a lead (or lead extension), according to the invention.

FIG. 7 is a schematic perspective, longitudinal cross-sectional, and transverse cross-sectional view of another embodiment of a conductive contact 702. The conductive contact 702 includes an adhesive aperture 704 defined along a longitudinal length, represented by arrow 706, of the conductive contact 702. The adhesive aperture 704 includes a recess 708 with a first opening 710 defined in the recess 708. It will be understood that a plurality of adhesive apertures 704 may be defined in the conductive contact 702. In at least some embodiments, the first opening 710 is configured and arranged to receive a conductor. In at least some embodiments, the first opening 710 is defined at one end of the recess 708. In at least some embodiments, the adhesive aperture 704 defines a second opening 712 defined in the recess 708. In at least some embodiments, the second opening 712 is defined at an opposite end of the recess 708 from the first opening 710. It will be understood that, in at least some embodiments, the conductive contact 702 includes a plurality of adhesive apertures 704.

Figure 8A:
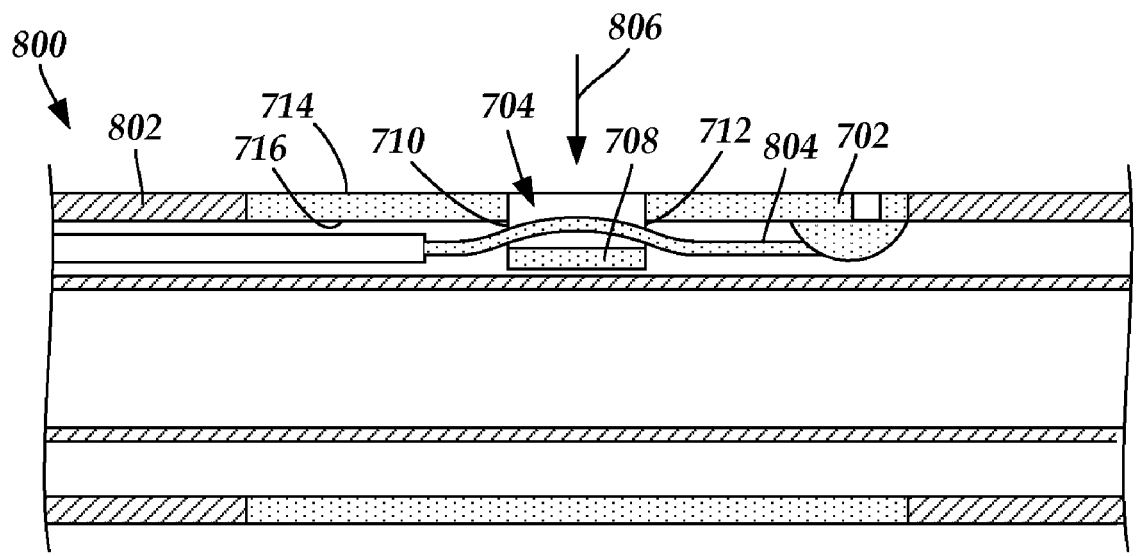
FIG. 8A is a schematic longitudinal cross-sectional view of one embodiment of the conductive contact of FIG. 7 disposed over an outer portion of a lead (or lead extension), a conductor disposed within the lead (or lead extension) electrically coupled to an inner surface of the conductive contact, according to the invention.

FIG. 8A is a schematic longitudinal cross-sectional view of one embodiment of a portion of a body 802 of an elongated member 800. The conductive contact 702 is disposed along an outer surface of the body 802. A conductor 804 is disposed in the body 802 and is electrically coupled to the inner surface 716 of the conductive contact 702. The conductor 804 extends through openings 710 and 712 defined in the adhesive aperture 704. In at least some embodiments, the conductor 804 extends through the openings 710 and 712 defined in the adhesive aperture 704 such that a portion of the conductor 804 extends across the recess 708 of the adhesive aperture 704, thereby exposing the portion of the conductor 804 to the outer surface 714 of the conductive contact 702. In at least some embodiments, an adhesive may be disposed in the recess 708 of the adhesive aperture 704, as shown by directional arrow 806, and allowed to cure, thereby adhesively coupling (e.g., mechanically coupling, electrically coupling, or both) the conductor 804 to the conductive contact 702.

Figure 8B:
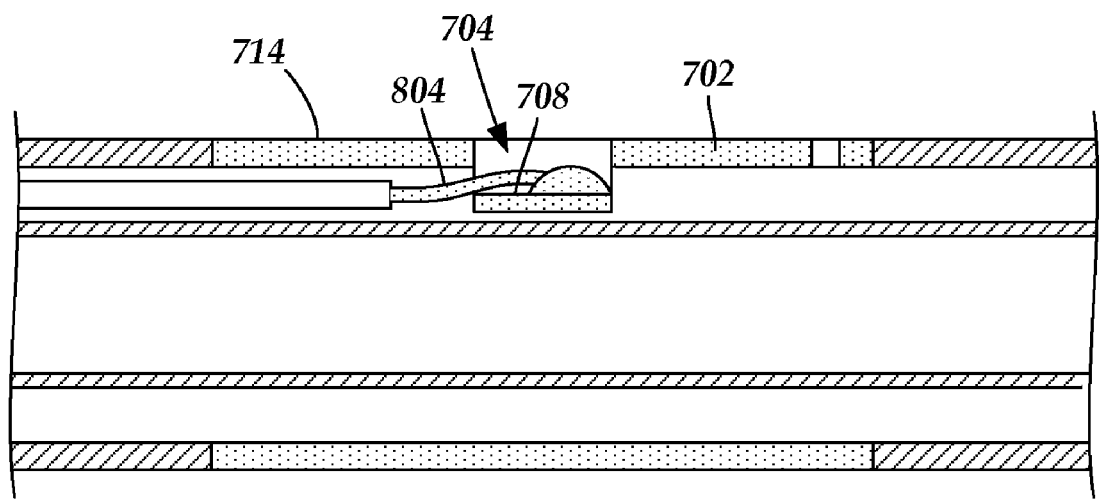
FIG. 8B is a schematic longitudinal cross-sectional view of the embodiment of the conductive contact of FIG. 7 disposed over an outer portion of the lead (or lead extension) of FIG. 8A, a conductor disposed within the lead (or lead extension) electrically coupled to a recess defined in an outer surface of the conductive contact, according to the invention.

When the conductive contact 702 is disposed on the elongated member 800, the conductor 804 disposed within the elongated member 800 is extended out through the first opening 710 of the adhesive aperture 704. As shown in FIG. 8B, in some embodiments the conductor 804 is electrically coupled to the recess 708 defined in the outer surface 714 of the conductive contact 702. As shown in FIG. 8A, in other embodiments the conductor extends back through the adhesive aperture 704 and electrically couples to an inner surface 716 of the conductive contact 702. In at least some embodiments, the conductor is extended back through the adhesive aperture 704 through the second opening 712 defined in the adhesive aperture 704.

Once the conductor 804 is electrically coupled to the conductive contact 702 (on either the inner surface 716 or the outer surface 714 of the conductive contact 702), adhesive may be disposed in the recess 708 of the adhesive aperture 704, thereby adhesively coupling the conductor 804 to the conductive contact 702. In at least some embodiments, the conductor 804 is both mechanically and electrically coupled to the recess 708. It will be understood that the conductive contact 702 can define a plurality of adhesive apertures 704. When the conductive contact 702 defines a plurality of adhesive apertures 704, adhesive can be applied in proximity to each of the adhesive apertures 704 to adhesively couple the conductor 804 to each of the recesses 708 such that the conductor 804 is mechanically coupled to at least one of the recesses 708 and electrically coupled to at least one of the recesses, in any combination. For example, in at least some embodiments, the adhesive mechanically couples the conductor 804 to one of the recesses 708 and electrically couples the conductor 804 to the other of the recesses 708.

Figure 8C:
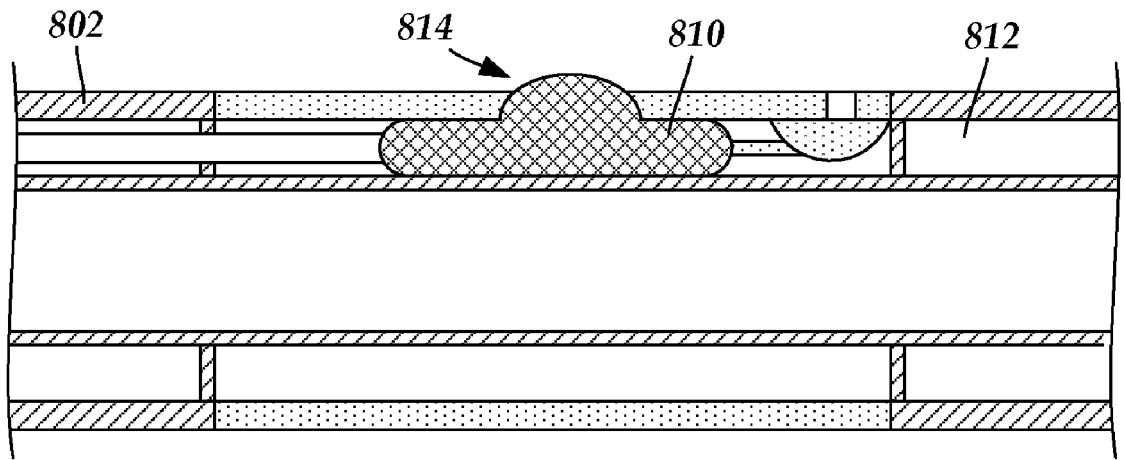
FIG. 8C is a schematic longitudinal cross-sectional view of one embodiment of the conductive contact of FIG. 7 disposed over an outer portion of the lead (or lead extension) of FIG. 8A and electrically coupled to a conductor disposed within the lead (or lead extension), the conductor also coupled to the lead (or lead extension), the conductive contact, or both, by an adhesive input through an adhesive aperture defined in the conductive contact, according to the invention.

FIG. 8C is a schematic longitudinal cross-sectional view of one embodiment of adhesive 810 disposed in the adhesive aperture (704 in FIG. 8A). In at least some embodiments, some of the adhesive 810 may flow through the one or more of the openings (710 and 712 of FIG. 8A) of the adhesive aperture (704 in FIG. 8A) and into the body 802, as discussed above, with reference to FIG. 6B. In at least some embodiments, at least a portion of the adhesive 810 flows into a lumen 812 of the body 802. In at least some embodiments, the adhesive 810 that flows into the body 802 may be contained by one or more seals formed during a reflow process, as discussed above, with reference to FIG. 6B.

Figure 8D:
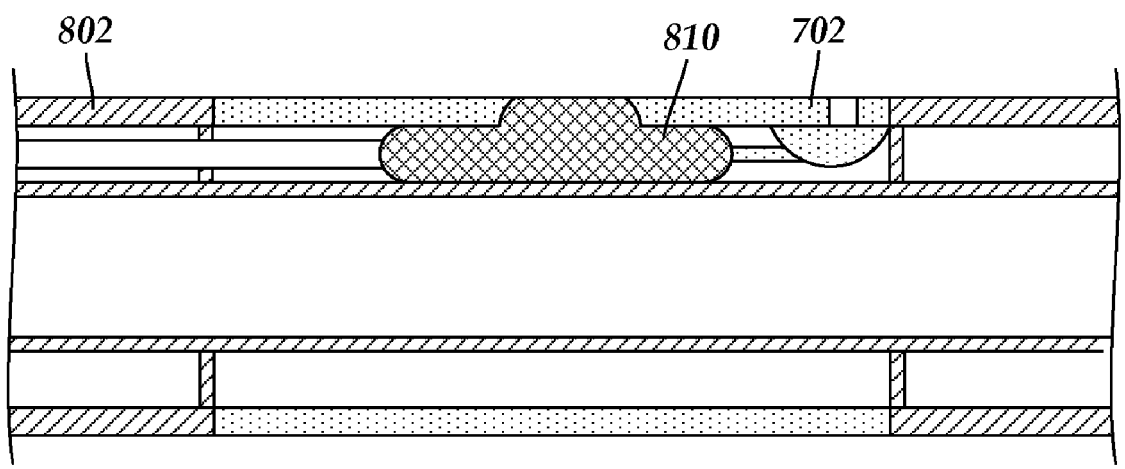
FIG. 8D is a schematic longitudinal cross-sectional view of one embodiment of the conductive contact of FIG. 7 disposed over an outer portion of the lead (or lead extension)of FIG. 8A, an outer surface of the lead (or lead extension) ground to remove portions of an adhesive extending outward from the adhesive aperture, according to the invention.

It may be an advantage for the body 602 or 802 to be isodiametric. In at least some embodiments, a portion 814 of the adhesive 610 or 810 may extend outward from the adhesive apertures 504 or 704, respectively, following the input of the adhesive 610 or 810 into the access apertures 504 or 704, respectively. In at least some embodiments, the portion 814 of the adhesive 610 and 810 extending from the adhesive apertures 504 or 704 may be removed. In at least some embodiments, the adhesive 610 and 810 is compatible with centerless grinding. Thus, in at least some embodiments when a portion 814 of the adhesive 601 or 810 extends from the adhesive apertures 504 or 704, respectively, the extending portions may be ground down. FIG. 8D is a schematic longitudinal cross-sectional view of one embodiment of the conductive contact 702 disposed along an outer surface of the body 802. The portion (814 in FIG. 8C) of the adhesive 810 extending from the adhesive aperture 804 has been ground down such that the body 802 is isodiametric.

Figure 9:
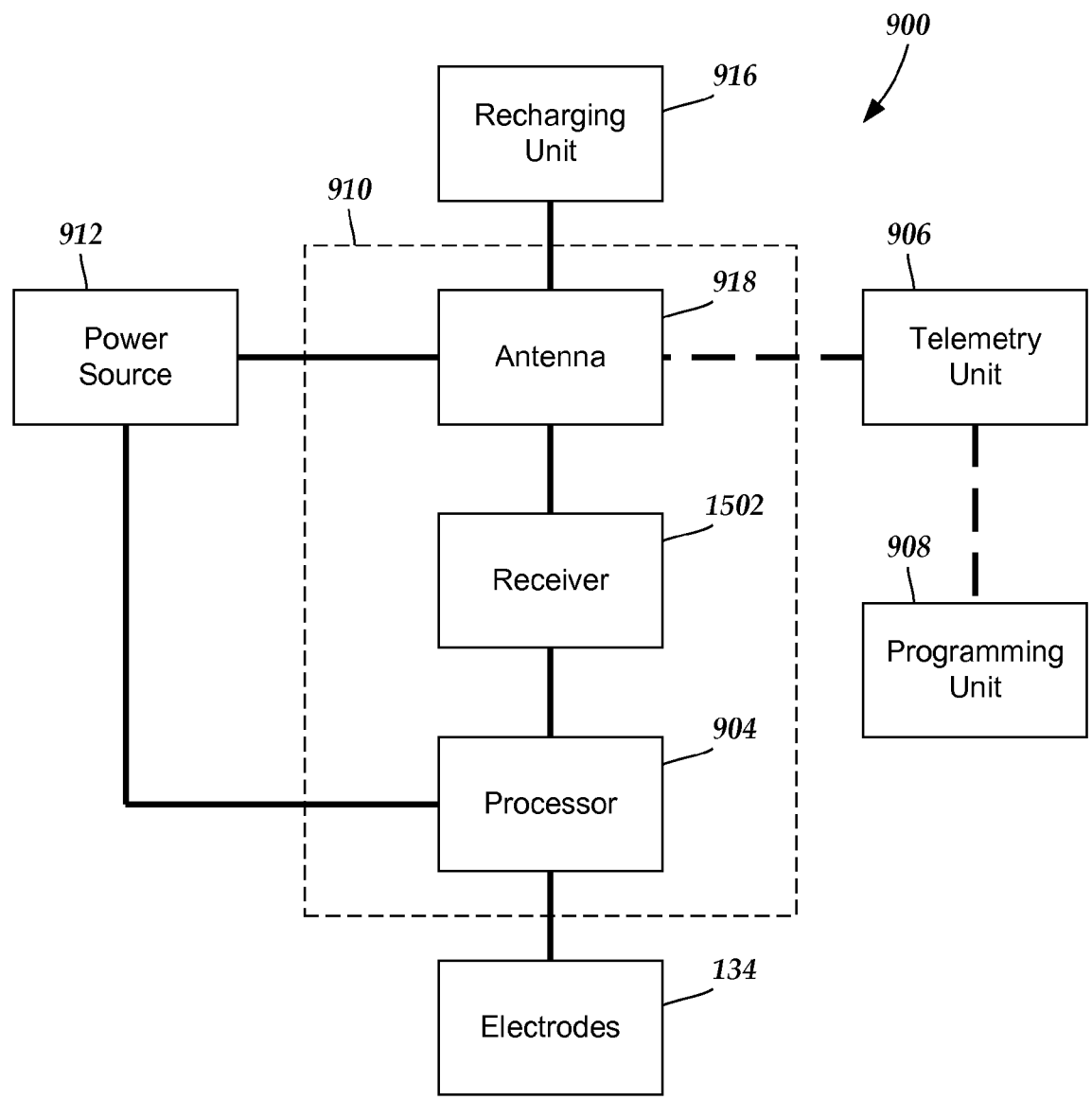
FIG. 9 is a schematic overview of one embodiment of components of a stimulation system, including an electronic subassembly disposed within a control module, according to the invention.

FIG. 9 is a schematic overview of one embodiment of components of an electrical stimulation system 900 including an electronic subassembly 910 disposed within a control module. It will be understood that the electrical stimulation system can include more, fewer, or different components and can have a variety of different configurations including those configurations disclosed in the stimulator references cited herein.

Some of the components (for example, power source 912, antenna 918, receiver 902, and processor 904) of the electrical stimulation system can be positioned on one or more circuit boards or similar carriers within a sealed housing of an implantable pulse generator, if desired. Any power source 912 can be used including, for example, a battery such as a primary battery or a rechargeable battery. Examples of other power sources include super capacitors, nuclear or atomic batteries, mechanical resonators, infrared collectors, thermally-powered energy sources, flexural powered energy sources, bioenergy power sources, fuel cells, bioelectric cells, osmotic pressure pumps, and the like including the power sources described in U.S. Patent Application Publication No. 2004/0059392, incorporated herein by reference.

As another alternative, power can be supplied by an external power source through inductive coupling via the optional antenna 918 or a secondary antenna. The external power source can be in a device that is mounted on the skin of the user or in a unit that is provided near the user on a permanent or periodic basis.

If the power source 912 is a rechargeable battery, the battery may be recharged using the optional antenna 918, if desired. Power can be provided to the battery for recharging by inductively coupling the battery through the antenna to a recharging unit 916 external to the user. Examples of such arrangements can be found in the references identified above.

In one embodiment, electrical current is emitted by the electrodes 134 on the paddle or lead body to stimulate nerve fibers, muscle fibers, or other body tissues near the electrical stimulation system. A processor 904 is generally included to control the timing and electrical characteristics of the electrical stimulation system. For example, the processor 904 can, if desired, control one or more of the timing, frequency, strength, duration, and waveform of the pulses. In addition, the processor 904 can select which electrodes can be used to provide stimulation, if desired. In some embodiments, the processor 904 may select which electrode(s) are cathodes and which electrode(s) are anodes. In some embodiments, the processor 904 may be used to identify which electrodes provide the most useful stimulation of the desired tissue.

Any processor can be used and can be as simple as an electronic device that, for example, produces pulses at a regular interval or the processor can be capable of receiving and interpreting instructions from an external programming unit 908 that, for example, allows modification of pulse characteristics. In the illustrated embodiment, the processor 904 is coupled to a receiver 902 which, in turn, is coupled to the optional antenna 918. This allows the processor 904 to receive instructions from an external source to, for example, direct the pulse characteristics and the selection of electrodes, if desired.

In one embodiment, the antenna 918 is capable of receiving signals (e.g., RF signals) from an external telemetry unit 906 which is programmed by a programming unit 908. The programming unit 908 can be external to, or part of, the telemetry unit 906. The telemetry unit 906 can be a device that is worn on the skin of the user or can be carried by the user and can have a form similar to a pager, cellular phone, or remote control, if desired. As another alternative, the telemetry unit 906 may not be worn or carried by the user but may only be available at a home station or at a clinician's office. The programming unit 908 can be any unit that can provide information to the telemetry unit 906 for transmission to the electrical stimulation system 900. The programming unit 908 can be part of the telemetry unit 906 or can provide signals or information to the telemetry unit 906 via a wireless or wired connection. One example of a suitable programming unit is a computer operated by the user or clinician to send signals to the telemetry unit 906.

The signals sent to the processor 904 via the antenna 918 and receiver 902 can be used to modify or otherwise direct the operation of the electrical stimulation system. For example, the signals may be used to modify the pulses of the electrical stimulation system such as modifying one or more of pulse duration, pulse frequency, pulse waveform, and pulse strength. The signals may also direct the electrical stimulation system 900 to cease operation, to start operation, to start charging the battery, or to stop charging the battery. In other embodiments, the stimulation system does not include an antenna 918 or receiver 902 and the processor 904 operates as programmed.

Optionally, the electrical stimulation system 900 may include a transmitter (not shown) coupled to the processor 904 and the antenna 918 for transmitting signals back to the telemetry unit 906 or another unit capable of receiving the signals. For example, the electrical stimulation system 900 may transmit signals indicating whether the electrical stimulation system 900 is operating properly or not or indicating when the battery needs to be charged or the level of charge remaining in the battery. The processor 904 may also be capable of transmitting information about the pulse characteristics so that a user or clinician can determine or verify the characteristics.

The above specification, examples and data provide a description of the manufacture and use of the composition of the invention. Since many embodiments of the invention can be made without departing from the spirit and scope of the invention, the invention also resides in the claims hereinafter appended.

What is claimed as new and desired to be protected by Letters Patent of the United States is:

1. An electrical stimulation lead comprising:
a lead body with a proximal end, a distal end, and a longitudinal length;
a plurality of conductive contacts disposed at the distal end and the proximal end of the lead body, the plurality of conductive contacts comprising
a plurality of electrodes disposed on the distal end of the lead, and
a plurality of terminals disposed on the proximal end of the lead,
wherein at least one of the conductive contacts is a first conductive contact that comprises a plurality of adhesive apertures and at least one contact aperture, the plurality of adhesive apertures and the at least one contact aperture each defined between an inner surface and an outer surface of the first conductive contact, wherein the plurality of adhesive apertures are longitudinally aligned along one side of the first conductive contact;
a plurality of conductors, each conductor electrically coupling at least one of the electrodes to at least one of the terminals, wherein each first conductive contact has at least one of the conductors associated with, and electrically coupled to that first conductive contact;
a weld disposed on the inner surface of the at least one first conductive contact in proximity to the at least one contact aperture of the at least one first conductive contact to electrically couple that first conductive contact to the at least one associated conductor; and a non-conductive adhesive disposed in proximity to the plurality of adhesive apertures of at least one first conductive contact to mechanically couple that first conductive contact to the at least one associated conductor.

2. The lead of claim 1, wherein the plurality of adhesive apertures comprises a recess in the outer surface of the at least one first conductive contact, the recess defining a first opening to the inner surface of the at least one first conductive contact.

3. The lead of claim 2, wherein the at least one associated conductor extends through the first opening from inside the lead body to the outer surface of the at least one first conductive contact.

4. The lead of claim 3, wherein the recess defines a second opening to the inner surface of the at least one first conductive contact, and wherein the at least one associated conductor extends through the second opening from the outer surface to the inner surface of the at least one first conductive contact.

5. The lead of claim 1, wherein the lead body defines at least one lumen through which the at least one associated conductor extends.

6. The lead of claim 5, wherein the adhesive is disposed in proximity to the plurality of adhesive apertures such that the adhesive is disposed in the lumen.

7. The lead of claim 6, wherein the adhesive is disposed in the lumen such that the adhesive is contained beneath the at least one first conductive contact by seals in the lumen at either end of the at least one first conductive contact.

8. The lead of claim 1, further comprising a conductor-carrying element extending along the longitudinal length of the lead body, the conductor-carrying element defining a plurality of conductor lumens.

9. The lead of claim 8, wherein the at least one associated conductor extends along at least a portion of at least one of the plurality of conductor lumens.

10. The lead of claim 1, wherein the lead body is isodiametric.

11. The lead of claim 1, wherein the first conductive contact is one of cylindrical shaped or C-shaped.

12. The lead of claim 1, wherein the plurality of adhesive apertures are longitudinally aligned with the at least one contact aperture along one side of the first conductive contact.

13. The lead of claim 1, wherein for each of the plurality of adhesive apertures an entire perimeter of the adhesive aperture is formed by the first conductive contact.

14. The lead of claim 1, wherein the non-conductive adhesive is disposed on the inner surface of the at least one conductive contact.

15. An electrical stimulating system comprising:
an electrical stimulating lead comprising a lead body with a proximal end, a distal end, and a longitudinal length;
a plurality of conductive contacts disposed at the distal end and the proximal end of the lead body, the plurality of conductive contacts comprising
a plurality of electrodes disposed on the distal end of the lead, and
a plurality of terminals disposed on the proximal end of the lead,
wherein at least one of the conductive contacts is a first conductive contact that comprises a plurality of adhesive apertures and at least one contact aperture, the plurality of adhesive apertures and the at least one contact aperture each defined between an inner surface and an outer surface of the first conductive contact, wherein the plurality of adhesive apertures are longitudinally aligned along one side of the first conductive contact;
a plurality of conductors, each conductor electrically coupling at least one of the electrodes to at least one of the terminals, wherein each first conductive contact has at least one of the conductors associated with, and electrically coupled to that first conductive contact;
a weld disposed on the inner surface of the at least one first conductive contact in proximity to the at least one contact aperture of the at least one first conductive contact to electrically couple that first conductive contact to the at least one associated conductor; and
a non-conductive adhesive disposed in proximity to the plurality of adhesive apertures of at least one first conductive contact to mechanically couple that first conductive contact to the at least one associated conductor;
a control module configured and arranged to electrically couple to the proximal end of the lead, the control module comprising
a housing, and
an electronic subassembly disposed in the housing; and
a connector for receiving the lead, the connector having a proximal end, a distal end, and a longitudinal length, the connector configured and arranged to receive the lead, the connector comprising
a connector housing defining a port at the distal end of the connector, the port configured and arranged for receiving the proximal end of the lead, and
a plurality of connector contacts disposed in the connector housing, the connector contacts configured and arranged to couple to at least one of the plurality of terminals disposed on the proximal end of the lead.

16. The electrical stimulating system of claim 15, further comprising a lead extension having a proximal end and a distal end, the connector disposed on the distal end of the lead extension.

17. The electrical stimulating system of claim 16, wherein the lead extension comprises:
a lead extension body with a proximal end, a distal end, and a longitudinal length;
a plurality of terminals disposed at the proximal end of the lead extension body, wherein at least one of the terminals is a first terminal that comprises at least one adhesive aperture and at least one contact aperture, the at least one adhesive aperture and the at least one contact aperture each defined between an inner surface and an outer surface of the first terminal;
a plurality of conductors, each conductor electrically coupled to art least one of the terminals, wherein each first terminal has at least one of the conductors associated, and electrically coupled, to that first terminal;
a weld disposed on an inner surface of the at least one first terminal in proximity to the at least one contact aperture of the at least one first terminal to electrically couple that first terminal to the at least one associated conductor; and
a non-conductive adhesive disposed in proximity to the at least one adhesive aperture of the at least one first terminal to mechanically couple the at least one first terminal to the at least one associated conductor.

* * * * *